United States Patent [19]
Christ

[11] Patent Number: 5,843,186
[45] Date of Patent: Dec. 1, 1998

[54] INTRAOCULAR LENS WITH ANTIMICROBIAL ACTIVITY

[75] Inventor: F. Richard Christ, Laguna Beach, Calif.

[73] Assignee: Implemed, Inc., Watertown, Mass.

[21] Appl. No.: 770,456

[22] Filed: Dec. 20, 1996

[51] Int. Cl.⁶ .................................................. A61F 2/16
[52] U.S. Cl. ................................................. 623/6; 604/20
[58] Field of Search ........................ 351/604; 623/4–6; 604/20

[56] References Cited

U.S. PATENT DOCUMENTS

| | | | |
|---|---|---|---|
| 4,486,416 | 12/1984 | Soll et al. | 424/180 |
| 4,613,665 | 9/1986 | Larm | 536/20 |
| 4,681,585 | 7/1987 | Sayano et al. | 623/6 |
| 4,707,471 | 11/1987 | Larm et al. | 514/54 |
| 4,723,950 | 2/1988 | Lee | 604/32 |
| 4,736,024 | 4/1988 | Della Ville et al. | 536/55.3 |
| 4,795,745 | 1/1989 | Larm et al. | 514/54 |
| 4,806,382 | 2/1989 | Goldberg et al. | 427/2 |
| 4,918,165 | 4/1990 | Soll et al. | 530/391 |
| 4,961,954 | 10/1990 | Goldberg et al. | 427/2 |
| 5,002,570 | 3/1991 | Sulc et al. | 623/6 |
| 5,037,435 | 8/1991 | Chang et al. | 623/6 |
| 5,041,133 | 8/1991 | Sayano et al. | 623/6 |
| 5,091,442 | 2/1992 | Milner | 523/122 |
| 5,094,876 | 3/1992 | Goldberg et al. | 427/2 |
| 5,108,776 | 4/1992 | Goldberg et al. | 427/2 |
| 5,130,160 | 7/1992 | Goldberg et al. | 427/2 |
| 5,135,540 | 8/1992 | Schepel et al. | 623/6 |
| 5,194,544 | 3/1993 | Goldberg et al. | 526/257 |
| 5,217,490 | 6/1993 | Sayano et al. | 623/6 |
| 5,304,182 | 4/1994 | Rheinish et al. | 606/107 |
| 5,306,297 | 4/1994 | Rheinish et al. | 623/6 |
| 5,320,843 | 6/1994 | Raheja et al. | 424/405 |
| 5,322,520 | 6/1994 | Milder | 604/20 X |
| 5,322,649 | 6/1994 | Rheinish et al. | 264/2.7 |
| 5,340,581 | 8/1994 | Tseng et al. | 424/401 |
| 5,340,583 | 8/1994 | Dziabo et al. | 424/412 |
| 5,358,688 | 10/1994 | Robertson | 422/28 |
| 5,376,115 | 12/1994 | Jansen | 623/6 |
| 5,405,386 | 4/1995 | Rheinish et al. | 623/6 |
| 5,416,205 | 5/1995 | Della Valle et al. | 623/6 X |
| 5,498,248 | 3/1996 | Milder | 604/20 X |
| 5,515,117 | 5/1996 | Dziabo et al. | 351/160 H |
| 5,520,664 | 5/1996 | Bricault, Jr. et al. | 604/265 |
| 5,536,861 | 7/1996 | Robertson | 556/419 |
| 5,554,187 | 9/1996 | Rizzo, III | 623/6 |
| 5,593,438 | 1/1997 | Akhavi et al. | 623/6 |
| 5,728,751 | 3/1998 | Patnaik | 623/6 X |

OTHER PUBLICATIONS

Encyclopedic Handbook of Biomaterials And Bioengieering, Part B: Applications, Chapter 46, Christ et al, "Biomaterials Used For Intraocular Lenses", Marcel Dekker, Inc., New York, 1995, pp. 1261–1281.

J. Cataract. Refract. Surg., vol. 22, Apr. 1966 Editor Note: "Endophthalmitis Following Cataract Surgery", pp. 279–280.

M. Busin, "Antibiotic Irrigation Of The Capsular Bag To Resolve Low–Grade Endophthalmitis", pp. 385–389.

P. Sioshansi, "New Process For Surface Treatment of Catheters", Artificial Organs, 18(4); 266–271, Blackwell Scientific Publications, Inc., Boston, 1994.

*Primary Examiner*—Mary Beth Jones
*Attorney, Agent, or Firm*—Pandiscio & Pandiscio

[57] ABSTRACT

An improved intraocular lens ("IOL") is provided that has antimicrobial properties. The invention involves use of one or more antimicrobial polymers in fabricating at least a portion of the IOL. A preferred form of the invention involves use of antimicrobial iontophoretic materials.

18 Claims, 3 Drawing Sheets

INTRAOCULAR LENS WITH ANTIMICROBIAL ACTIVITY

This invention relates to ophthalmic surgery and more particularly to provision of intraocular lenses (IOLs) having antimicrobial properties.

BACKGROUND

The mammalian eye comprises a transparent structure known as the crystalline lens that lies midway between the aqueous and the vitreous. Enclosing the lens is an elastic membrane called the lens capsule. As people age, pigments tend to build up in the lens and degeneration of the lens cells occurs. The degeneration leads to opacification of the lens and a condition known as a cataract. Less frequent causes of cataracts which can occur at any age are trauma to the head, exposure to certain types of electromagnetic radiation, diabetes, and congenital disease. When a cataract becomes dense enough it causes a decline in visual acuity. Currently cataract treatment consists of removing the crystalline lens and replacing it with an intraocular plastic lens. The latter is commonly identified by the acronym "IOL".

All IOLs consist of an optical lens portion and a portion used for stably positioning the IOL in alignment with the visual axis of the eye. The optical lens portion is commonly called the "optic" or "optical lens body". IOL designs are either optic/plate designs or optic/haptic designs, the terms "plate" and "haptic" referring to the form of the stabilizing or positioning portion of the IOL. In an optic/haptic design, the stabilizing or positioning portion of the IOL consists of two filament-like elements called "haptics". The primary function of the optic or lens body is to focus incoming light upon the retina, taking the place of the natural lens which has been removed in cataract surgery.

IOLs featuring the optic/plate design are usually constructed from one material, while IOLs embodying an optic/haptic design may be made of a single material or else the optic may be made of one material and the haptics may be made of a second material.

The IOLs are made of various materials, usually from a transparent polymeric plastic. The common single-piece design is usually made of an organic polymeric plastic, such as polymethymethacrylate ("PMMA") or silicone. In a three-piece IOL design (i.e., one comprising the optic plus two haptics), the optic is commonly made of a transparent plastic such as PMMA or silicone, while the haptics commonly are extruded filaments of PMMA, polypropylene ("PP") or polymerized vinylidene fluoride ("PVDF"). Other materials also have been used or suggested. The filamentary-like haptics are heat-formed into desired shapes and then are bonded to the optic or lens body.

IOLs also are categorized as foldable or non-foldable. Non-foldable IOLs are substantially rigid and are commonly made of PMMA, although non-foldable IOLs made of other plastics such as polycarbonate and polysulfone have also been made. Foldable IOLs are commonly made from silicone, acrylic or hydrogel elastomers. Foldable IOLs offer the advantage that they can be folded so that a smaller incision is required for their insertion into the eye than is the case with non-foldable IOLs.

Since the implantation of an IOL is an invasive surgical procedure, the potential exists for the introduction of micro-organisms into the eye and subsequent infection. The organisms may enter the eye through the wound, or be carried into the eye on the surface of the IOL as it brushes against the patient's eyelashes, ocular surface skin or other tissues immediately adjacent to the eye. Even careful attempts to isolate the eye in the surgical field cannot always or completely prevent the natural bacteria on a patient's eyelid, eyelashes and other immediately adjacent tissues from entering the eye during surgery, thereby establishing the basis for intraocular infection. The intraocular infection is termed "endophthalmitis", which can be devastating if not caught immediately and properly treated.

Acute endophthalmitis occurs within days of surgery and usually is the result of Staphylococcus epidermidis infection. Delayed-onset endophthalmitis occurs several weeks to months after surgery and is the result of Staphylococcus epidermis or Propionibacterium acnes infection. Delayed-onset endophthalmitis is caused by lower virulence organisms that "smolder" for a period of time before a stimulus causes them to flare up (e.g., trauma, laser surgery, etc.).

In modern cataract surgery carried out in sterile surgical suites, the occurrence of endophthalmitis is low, currently approximately 0.1% in the U.S. However, given that currently approximately 1.7 million cataract surgeries are performed in the U.S.A. annually, this "low" rate means 1000–2000 real cases of endophthalmitis per year. In other parts of the world where less modern surgical facilities, equipment and techniques are common, the incidence of such potentially devastating infections is probably much greater.

In modern cataract surgery practice care is taken not to contact the IOL with any surface that might be contaminated, in order to avoid adsorption of bacteria onto the surface of an IOL. However, despite the best sterilization and aseptic techniques, it is difficult to avoid some surface contact when using forceps or other insertion tools to implant an IOL. Accordingly it is common for an antibiotic drug to be given prophylactically as drops applied to the eye or as additions to intraoperative irrigation solutions to minimize the odds of infection. The success of this approach is critically dependent on the compliance of the nurses in adding antibiotics to solution bottles or of the patients in properly using the eyedrops.

The IOL haptics are a common locus for colonizing bacteria and other microbes. Investigations have produced scanning electron micrographs ("SEMS") showing bacteria embedded in a biofilm on the haptic surfaces. See L. A. Wilson, "Biomaterials And Ocular Infection", Chapter 16 in J. S. Pepose et al, "Ocular Infections And Immunity", Mosby, St. Louis, 1996 p.227; and B. Jansen et. Al., "Late Onset Endophthalmitis Associated With Intraocular Lens: Case of Molecularly Proved S. epidermidis Aetology", Br. J. Ophthalmol., 75(1991, 440–441. Some investigators have reported greater bacterial adherence to PP than to PMMA. Others have studied bacterial adherence to optic materials and have suggested that bacteria are more adherent to silicone than to PMMA or the newer foldable acrylic elastomers.

In modern implant surgery the IOL implant site is usually the capsular bag, which is a likely site for microbial colonization. Organisms adherent to insertion instruments (e.g., forceps, inserters, etc.) have the potential to infect the capsular bag as well as other portions of the intraocular cavity. Treatment of infections in the capsular bag is a problem because of the difficulty of providing access thereto of suitable antibiotics and also because the relatively quiescent environment favors biofilm formation and microbial colonization.

Accordingly there is a need for an improved method of preventing or reducing the incidence of endophthalmitis in relation to IOL implantation.

OBJECTS AND SUMMARY OF THE INVENTION

The primary object of this invention is to provide a new and improved means for preventing or reducing the incidence of both acute and late-onset endophthalmitis in connection with IOL implantations.

Another object is to provide a new and improved means for preventing microbial colonization on an implanted IOL and in the medium surrounding the implanted IOL.

Still another object is to provide a new and improved means for releasing an antimicrobial agent into the medium surrounding an implanted IOL.

A further more specific object is to provide a new and improved mode of releasing an antimicrobial agent in the capsular bag to destroy or prevent colonization of microorganisms that are carried into the bag by an implanted IOL or a surgical instrument used for such implantation or by direct inoculation.

Another object is to improve on IOL surgery by introducing an antimicrobial agent to the surgical site by means of the implanted IOL.

A further object is to provide new and improved IOL designs having antimicrobial properties.

These and other objects are achieved by providing IOLs that comprise, at least in part, a material that has an inherent resistance to microbial colonization and also the potential to release an antimicrobial agent into the surrounding medium. More specifically the invention comprises fabricating IOLs from polymeric materials that are loaded with or comprise one or more antimicrobial components.

The IOLs provided by this invention comprise haptics and/or optic bodies that are characterized by at least one antimicrobial species that is leachable into or otherwise contacts the aqueous environment immediately surrounding the surgical optical site, whereby to kill circulating organisms. The antimicrobial species are compatible with the polymers that make up the haptic components or the optic bodies of the IOLs and will not degrade mechanical performance of the IOLs at the additive levels required for effective antimicrobial action.

The IOLs may be foldable or non-foldable. In a preferred embodiment, only the haptics of the IOL are characterized by antimicrobial properties. In another embodiment the IOLs have an optic portion that comprises in part a material having antimicrobial properties. The IOLs of this invention are benign with respect to intraocular tissues, e.g., the trabeculum and corneal endothelium, and the antimicrobial agent will not accumulate in any tissues but instead will tend to be freely eliminated from the intraocular environment.

Preferably the invention involves provision of IOLs using antimicrobial polymers that are the same as or function like the antimicrobial iontophoretic materials that are disclosed in U.S. Pat. Nos. 5,322,520 and 5,498,248, both issued to Fredric L. Milder for "Iontophoretic Structure For Medical Devices". The information disclosed by said U.S. Pat. Nos. 5,322,520 and 5,498,248 is incorporated herein by reference thereto. Other antimicrobial compositions also may be used in practicing this invention.

More specifically, in its preferred embodiments, this invention involves making at least part of each IOL from a composite iontophoretic material which comprises two different galvanic potential components embedded in and separated by a conductive polymer matrix, whereby when the IOL is implanted into an eye, the saline fluid in the eye acts as an electrolytic fluid medium to complete a circuit between the two galvanic potential components, causing ions of one of the components to be driven into solution where they have an antibacterial effect. The two different galvanic potential components are metals introduced into the conductive polymer matrix as powders. The polymer matrix may be inherently conductive or it may be rendered conductive by addition of a conductive material.

In one selected embodiment, an IOL has haptics that are formed of a composite iontophoretic material that comprises first and second metals with different galvanic potentials disposed in a conductive polymer matrix, whereby when the IOL is implanted in an eye in contact with the saline fluid in the eye, a current flow is created which injects anti-bacterial oligodynamic metal ions into the solution.

In another embodiment, the IOL is formed with an optic that comprises a transparent center lens portion that is non-iontophoretic and a rim portion that is made of an opaque or transparent iontophoretic material.

In a further embodiment the composite iontophoretic material is coated over an existing portion of the IOL.

Still other embodiments of the invention involve use of non-iontophoretic antimicrobial compositions for manufacturing the haptics, with certain of said non-iontophoretic antimicrobial compositions also being used to fabricate all or only rim portions of the optical lens body.

Other features of the invention are described or rendered obvious by the following detailed description which is to be considered together with the accompanying drawings.

DETAILED DESCRIPTION OF THE INVENTION

Certain oligodynamic metals, such as silver are effective in minute quantities as bacteriostats and bactericides. The most active form of these oligodynamic metals is as ions in solution. While the precise nature of the bactericidal effect is unknown, it is believed to involve altering the function of the cell membrane or linking to the cell's DNA to disrupt cell function. The bactericidal action of oligodynamic metals is effective against a broad spectrum of bacteria, including substantially all of the common strains which cause infection. When these metals are used in the minute concentrations required to kill or stem the growth of bacteria, they do not have any detrimental effect on normal mammalian cells.

Silver is used routinely in antibacterial salves, such as silver sulfadiazine, and has also been used in clinical trials to coat gauze for burn dressings. Silver also has been used as a bacteriostat in various medical devices that are applied to a human body. For example, catheters having silver impregnated in a soluble collagen or polymer coating are also known. After these catheters are in place, the coating slowly dissolves and the silver is released over time into the patient. The infection rates with these products are reported to be two to four times lower than standard catheters.

However, many catheters that use oligodynamic metals as bacteriostats fail to adequately prevent infection for one or more of the following reasons: 1) Silver released from soluble coatings is not always in the same charge state and often is not charged at all, therefore its bactericidal potential is not optimized; 2) With soluble-coated catheters, once the coating dissolves, usually over about two weeks, there is no further antibacterial protection; 3) A non-soluble silver, silver alloy or silver-oxide coating can prevent colonization of the catheter to a limited extent, but the oligodynamic metal is not released into the surrounding fluid or tissue; 4) Due to the substantial change in the catheter placement procedure, the use of these catheters requires additional personnel training; and 5) Although infection can enter the body through either the interior or the exterior of the catheter, not all catheters provide both interior and exterior protection. Furthermore, despite the capability of silver alloy-coated devices to produce a two to four fold reduction in bacterial colonization, their high cost greatly detracts from their modest capabilities.

Research from the 1970's onward has been directed toward improving the antibacterial effects of oligodynamic metals by electrically injecting the metal ions into solution. This process, known as "oligodynamic iontophoresis", involves moving ions in a conductive fluid environment under the influence of a low strength electric field and forcing the ions into a conductive fluid environment using minute electric currents. For example, if two electrodes made of a metal, such as silver, are introduced into a conductive medium, such as saline, blood or urine, and an electrical potential is applied across the electrodes, silver ions are driven into solution creating an enhanced bactericidal effect. The current required to safely drive a sufficient amount of silver ions into solution to control infection is in the range of 1 to 400 microamperes. This current range does not cause localized cell necrosis and is below the sensory or pain threshold. It has been reported that this process offers the potential of reducing bacterial colonization fifteen to one hundred fold.

Despite its great potential, the oligodynamic iontophoresis phenomenon has found limited use in conjunction with medical devices. One reason was the apparently essential need for electrodes in a conductive medium and an external electric power supply for driving the electrodes.

However, U.S. Pat. Nos. 5,322,520 and 5,498,248, both issued to Fredric L. Milder and both entitled "Iontophoretic Structure For Medical Devices", disclose antimicrobial polymer technology whereby "oligodynamic iontophoresis" is effected by a material comprising a conductive organic polymer matrix in which is suspended a combination of first and second metals that has a chemical half-cell potential difference. This composite material, hereinafter described or identified as an "iontophoretic" material, acts as a multiple of minute electrochemical cells in which a voltage potential generated between the dissimilar metals generate a current of electrons in the conductive matrix upon exposure of the composite material to an electrolyte solution such as saline or body fluids. The electron current flow results in the release of metal ions into the conductive electrolyte fluid by iontophoresis. In the case of a composite material comprising silver and platinum, the flow of electrons results in the liberation of silver ion ($Ag^+$) to the polymer surface and ultimately the surrounding medium. The silver ions act as a potent bactericide and fungicide.

Figure 1:
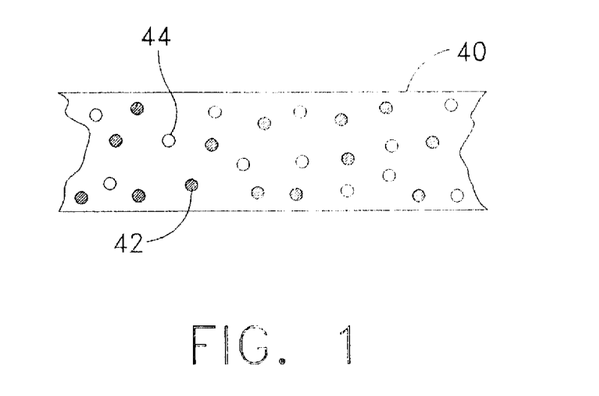
FIG. 1 is a sectional view of an iontophoretic polymer material as used in practicing this invention.

FIG. 1 is a fragmentary sectional view of a body of a composite material having iontophoretic properties. In this case the composite material comprises a polymer matrix 40 in which are dispersed two dissimilar metals 42 and 44, e.g., silver and platinum. The base polymer material is electrically conductive to the extent required for this invention.

Figure 2:
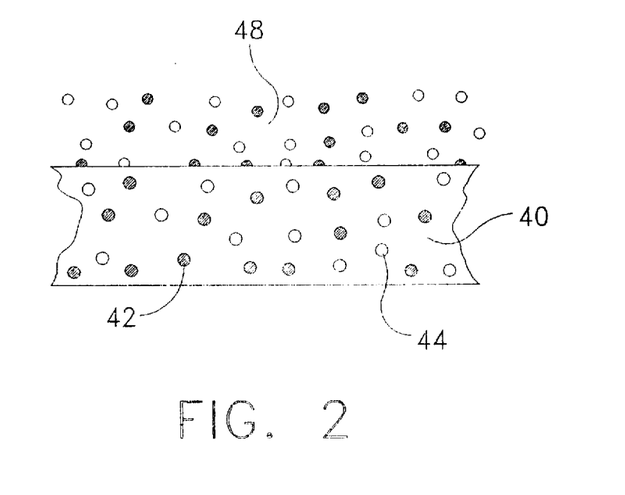
FIG. 2 depicts the iontophoresis effect created when the iontophoretic polymer material is contacted with a fluid electrolyte.

FIG. 2 illustrates the iontophoresis effect created by the composite material 40, 42, 44 when placed in contact with an electrolytic fluid (not shown) such as saline fluid in the eye. The first and second metal powders 42, 44 act as electrodes and create a voltage potential therebetween, whereby electrons migrate through the base polymer 40 and generate an electric current. Metal ions 48 are thus driven into the conductive fluid (not shown) by iontophoresis. The magnitude of the electric current is regulated by the quantity and nature of the dissimilar metal powders embedded in the base polymer material 40 and by the conductivity of that base polymer material.

In accordance with this invention, IOLs including those shown in FIGS. 3 to 6, are imparted with anti-microbial properties by making some or all of the IOL of a polymer material that comprises an antimicrobial agent that is released into the aqueous environment immediately surrounding the IOL. Alternatively, as described hereinafter (see FIG. 8) the invention may be practiced by coating at least a portion of the IOL with an antimicrobial material. Preferably, but not necessarily (depending upon the IOL design), the antimicrobial polymer is an iontophoretic material as disclosed by said Milder U.S. Pat. Nos. 5,322,520 and 5,498,248.

Figure 3:
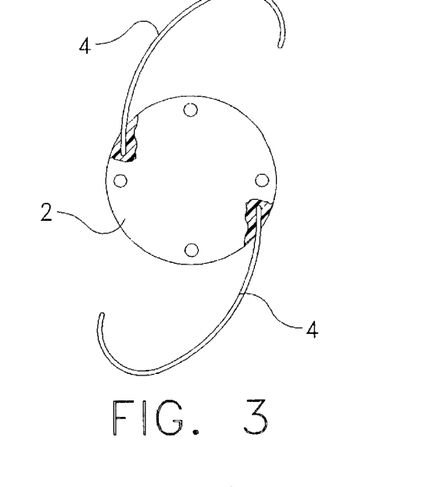
FIG. 3 is a front elevational view of one form of a known implantable intraocular lens.
Figure 3A:
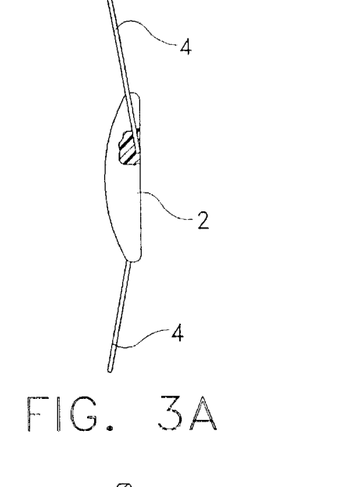
FIG. 3A is a side elevational view of the implantable intraocular lens depicted in FIG. 3.

FIGS. 3 and 3A illustrate a well-known three-piece posterior chamber IOL design that comprises an optical lens body 2 that is made of relatively stiff transparent material such as PMMA and a pair of curved flexible haptics 4. Heretofore a common practice has been to make the lens body 2 of a material such as PMMA and the haptics 4 of a different material, e.g., polypropylene ("PP"). This particular well-known form of IOL is non-foldable in the sense that the PMMA lens body is sufficiently stiff as to be non-foldable. In accordance with the preferred mode of practicing this invention, the design of FIGS. 1 and 1A is implemented by making the lens body 2 of a transparent, non-antimicrobial polymer material such as PMMA, while the haptics are made of an anti-microbial material. Preferably the haptics are made of an iontophoretic material such as the ones disclosed by the Milder patents cited supra.

Figure 4:
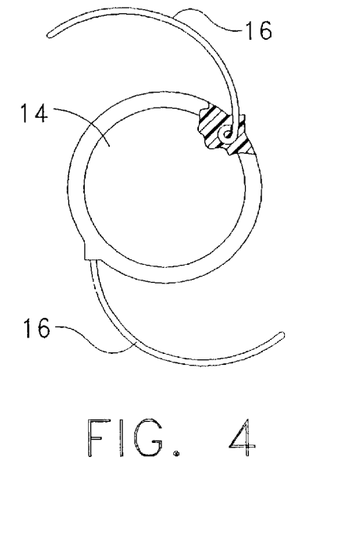
FIG. 4 is a front elevational view in partial section of a second form of a known implantable intraocular lens.
Figure 4A:
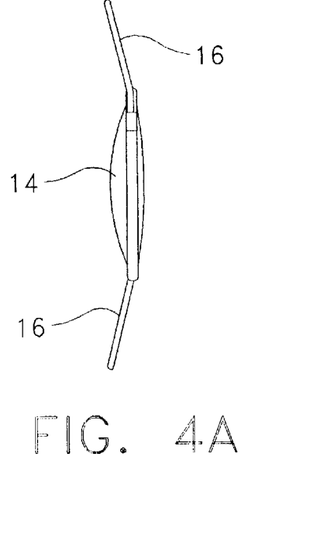
FIG. 4A is a side elevational view of the implantable intraocular lens depicted in FIG. 4.

FIGS. 4 and 4A illustrate a three-piece posterior chamber IOL design that comprises a central optics portion (lens body) 14 which typically is made of silicone and is foldable, plus a pair of haptics 16 similar to the haptics shown in FIGS. 1, 1A. Heretofore haptics 16 have been made of polypropylene or other material such as extruded PMMA. Alternatively and heretofore, the design shown in FIG. 4 has been formed with an optics section 14 made of an bendable acrylic polymer. In the design shown in FIG. 4 the maximum diametral distance between the ends of the two haptics usually is approximately 13 mm. The particular design shown in FIGS. 4 and 4A is essentially disclosed by U.S. Pat. No. 4,790,846, issued 13 Dec. 1988 to F. Richard Christ, D. K. Pettit and J. C. Day.

In accordance with this invention, the design of FIGS. 4 and 4A is implemented by making the lens body 14 of a transparent, non-antimicrobial polymer material such as PMMA or silicone, while the haptics are made of a selected antimicrobial material. Preferably the haptics are made of an iontophoretic material such as the ones disclosed by the Milder patents cited supra. Of course, the lens body 14 may also be made of an antimicrobial material, but only if the antimicrobial material is transparent to light.

Figure 5:
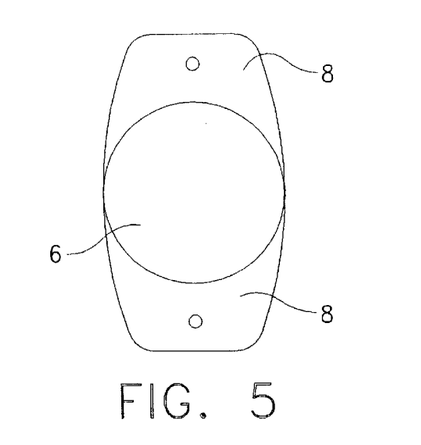
FIG. 5 is a front elevational view of a third form of a known implantable intraocular lens.
Figure 5A:
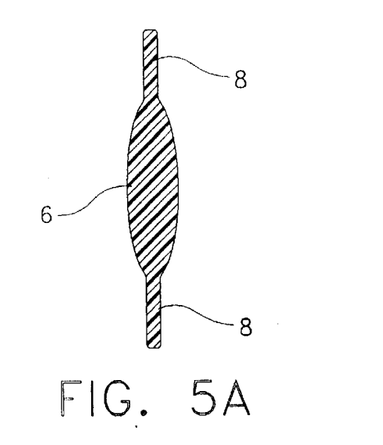
FIG. 5A is a sectional side elevational view of the implantable intraocular lens depicted in FIG. 5.

FIGS. 5 and 5A illustrate a one-piece foldable plate-type posterior chamber IOL design comprising an optic body 6 and a pair of diametrically opposed plate sections 8 that serve to position the IOL in the eye. IOLs embodying this particular design typically are made of silicone (essentially an elastomer) and hence they are foldable. The distance between the extremities of the two plate sections 8 is approximately 10 mm, while conventionally the maximum distance between the apices of the two haptics 4 in the FIG. 3 embodiment is typically about 13 mm.

Figure 6:
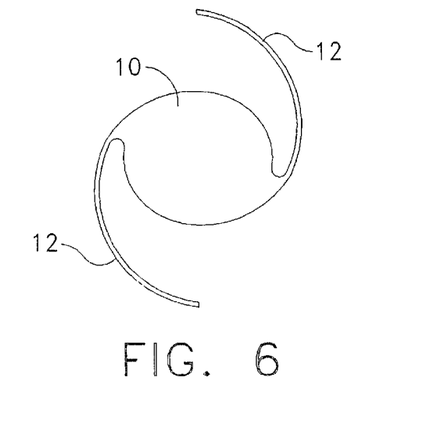
FIG. 6 is a front elevational view of a fourth form of a known implantable intraocular lens.
Figure 6A:
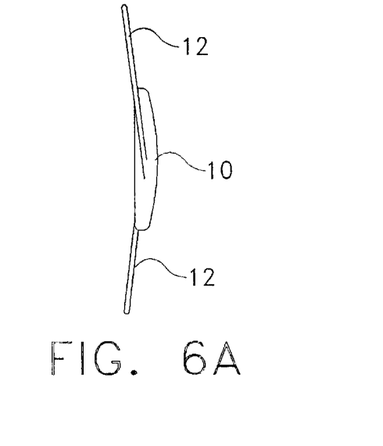
FIG. 6A is a side elevational view of the implantable intraocular lens depicted in FIG. 6.

FIGS. 6 and 6A illustrate a one-piece posterior chamber IOL design that comprises an optic or lens body 10 and a pair of helically shaped haptics 12. Commonly this type of IOL is made of PMMA, with the optic body being substantially rigid or stiff and the haptics being relatively flexible due to their relatively small cross-sectional diameter. In this particular design, the maximum diametral distance between the ends of the haptics is approximately 13 mm.

Iontophoretic materials made as disclosed by Milder U.S. Pat. Nos. 5,322,520 and 5,498,248 tend to be opaque and hence they cannot be used for the IOL optical zone that is required to focus incoming light on to the retina. More specifically, such materials cannot be used for the one-piece designs shown in FIGS. 5, 5A and 6, 6A (they also cannot be used for the central optics portions of the designs shown in FIGS. 3 and 4).

Accordingly, in the case of single piece IOL designs as shown in FIGS. 5, 5A, 6 and 6A, the required anti-microbial property is achieved by making the one-piece IOL of a selected polymeric material that is transparent and also includes an antibacterial agent that is leachable into the surrounding tissue and aqueous environment. Materials suitable for this purpose are described hereinafter.

Figure 7:
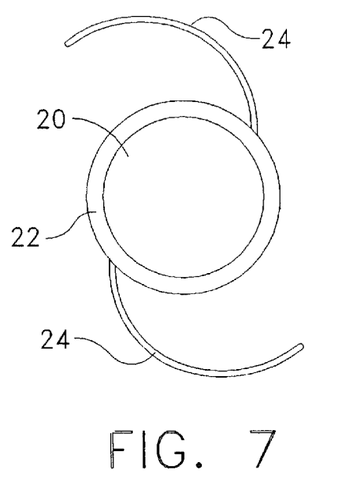
FIG. 7 illustrates a modified form of IOL incorporating the present invention.
Figure 7A:
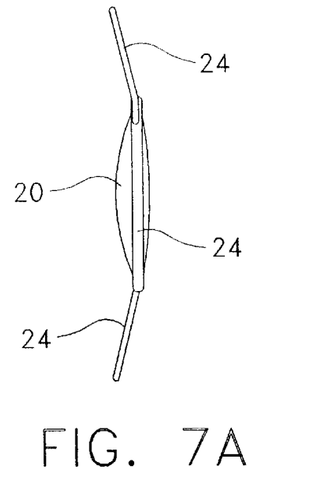

FIG. 7 is a variation of the embodiment of FIG. 4. In this case, the IOL design features a central lens section (lens body) 20 that is made of a polymer that lacks anti-microbial properties but is highly transparent and characterized by the proper refractive index, plus a rim section 22 that comprises a material that has anti-microbial properties according to the present invention. The central lens and rim sections 20 and 22 may be preformed separately and then the rim section may be positioned around and bonded to the central lens section 20. Alternatively the rim section may be preformed and then the central lens section may be formed and bonded to the rim section by molding the central lens section in situ, i.e., by molding it in the area defined by the inner edge of the rim section. A further alternative is to form the central lens section first and then mold the rim portion in place around the preformed central lens section. In any event this embodiment also includes two haptics 24 that are curved like the ones shown in FIGS. 3, 4 and 6. The haptics may be made of the same or a different material than the rim section. Preferably haptics 24 are made of an antimicrobial polymer material like the rim section. The haptics may be formed separately and then attached to the rim section. Preferably they are made of the same material as the rim section and are formed simultaneously and integral with the rim section. The haptics and the rim sections may be made of an iontophoretic polymer as described by the Milder patents cited hereinabove, or an antimicrobial non-iontophoretic polymer material as described hereinafter.

If a polymeric iontophoretic material having antimicrobial properties is rendered conductive as required for the purposes of this invention by the addition of a material such as carbon that renders the polymer opaque or translucent, then the resulting antibacterial iontophoretic polymer may not be used for the optic section of the IOLs but instead may be used only for the rim section and haptics of the embodiment of FIG. 7 or the haptics of the designs of FIGS. 3 and 4 or the plate sections 8 of FIG. 5.

Of course, if this invention is practiced using an antimicrobial polymer that is not iontophoretic and also is transparent, then all of the component parts of the various embodiments shown in the drawings, notably the embodiments of FIGS. 3, 4 and 7, may be made of that antimicrobial polymer.

For the purposes of this invention, the iontophoretic anti-microbial polymers may take the form of a composite material comprising galvanic metal components in a conductive polymer matrix that may (but need not) have elastomeric properties. More specifically, the polymeric matrix base for the iontophoretic composite material may comprise a polyester, polyethylene, PMMA, polypropylene, polytetrafluoroethylene (Teflon®), and polyvinylchloride (PVC) and/or silicone. In the case of those polymer base materials, the required conductivity (resistivity) is achieved by loading the polymer (or monomer, depending on the procedure for making the polymer with anti-microbial properties) with carbon or other conductive filler in particle form.

The invention also contemplates the use of naturally conductive polymers as the base material for producing suitable antimicrobial iontophoretic polymer materials. In the case of certain grades of polyvinylidene fluoride, the addition of carbon or other conductive filler may be omitted or, depending on the desired conductivity, a lesser amount of carbon or other conductive filler is used than is the case when modifying a silicone or a polyvinyl, polyester, or polyethylene base material to achieve the desired conductivity. Use of a transparent polymer that is naturally conductive is an advantage in that it avoids the need to add a filler such as carbon that is opaque and hence tends to affect the light transmissibility of the polymer. Antibacterial polymers that are loaded with carbon to render them conductive may be used only for the positioning haptic portions of IOLs of the general type shown in FIGS. 3 and 4 or, in the case of the design shown in FIG. 7, only for the rim portion and the haptics.

With regard to the metals that are used to provide the necessary galvanic action for the iontophoretic materials, a preferred combination of first and second metal powders having an electrical half-cell potential difference comprises silver and platinum. However, the invention contemplates that the silver and platinum combination may be replaced by other possible combinations, e.g., silver and gold, or silver and copper, or copper and platinum. The combination of silver and copper promises greater bactericidal activity than the combination of silver and platinum, and also copper is a less costly metal than platinum. However, the combination of silver and platinum is preferred from a safety standpoint because the natural chloride content of the aqueous humor tends to provide a desirable limit on the silver ion concentration in the eye. These metal powder combinations are mixed into the base polymer at relatively low volume concentrations, and the addition of such metals is generally conducted prior to fabrication (by extrusion or compression molding or other manufacturing process) of the IOL or its anti-bacterial component. Although the use of silver, platinum and gold involves relatively expensive materials, it is to be appreciated that they are used in such minute quantities that their use does not adversely impact the overall cost of the IOL that embodies same.

Although the preferred mode of practicing the invention consists of making the haptics or the annular rim section of the optic (FIG. 7) of an iontophoretic polymer (or some other non-iontophoretic antimicrobial material as hereinafter described) it is recognized also that similar results can be achieved by finish coating the haptics or plates of the IOLs shown in FIGS. 3–6, or the rim section of the IOL shown in FIG. 7, with a desired composite polymer having antimicrobial properties.

Figure 8:
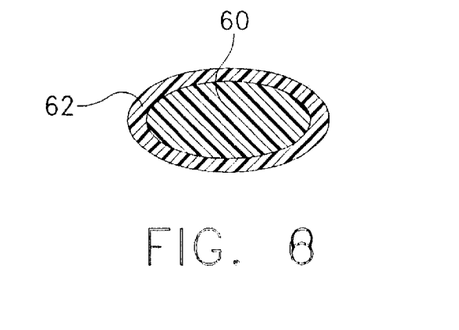
FIG. 8 is a cross-sectional view of a haptic formed according to this invention.

Thus, as shown in FIG. 8, for example, the haptics may comprise a central portion 60 made of a plastic such as PMMA or polypropylene that lacks anti-microbial properties, but has a coating 62 that is made of an antimicrobial material, e.g., an iontophoretic polymer material as disclosed hereinabove or by Milder, or some other antimicrobial material. In such case, the coating 62 functions to provide the desired bacteriostatic action.

Although various oligodynamic metals have been disclosed by the Milder patents, it should be understood that other metals also have antimicrobial properties. Hence for the purposes of this invention, the following metals appear to qualify as providing antimicrobial properties: chromium, zirconium, aluminum, nickel, tungsten, molybdenum, tantalum, platinum, palladium, iridium, gold, silver, mercury, copper, and zinc.

It is to be noted that blood or a saline solution functions as an electrolyte. Therefore, when an IOL made in accordance with this invention using an iontophoretic antimicrobial polymer is contacted with aqueous humor or eye tissue containing blood or saline, the two dissimilar metal powders, e.g., silver and platinum in the conductive iontophoretic polymer portion of the IOL, become an array of small batteries. Specifically, each powdered metal granule embedded in the base polymer material that makes contact with the electrolytic blood or saline becomes either an anode or a cathode, depending on the particular metals chosen as the first and second metal powders.

As noted previously the electric current is regulated by the quantity and nature of the dissimilar metal powders embedded in the base material 40 and by the conductivity of the base material. These factors are adjusted so that the current and ultimate metal ion densities are in an efficacious and safe range according to the teachings of said U.S. Pat. Nos. 5,322,520 and 5,498,248 (see column 5, lines 45–67 and column 6, lines 1–20 of the latter patent).

The metal powders in the iontophoretic material may, but need not, be of the same granular size and of the same volume loading. Preferably the metal particles loading of the conductive polymer is such as to provide a current density of between $10^{-8}$ to $10^{-6}$ amperes per mm$^2$, which range is sufficient to be bacteriostatic or bactericidal and yet not so high as to cause pH changes or other deleterious mammalian cell reactions. This current density can be varied by changing the metals, varying the amount of the metals embedded in the polymer matrix, and also the thickness of the portions of the IOL that are made with said iontophoretic materials. A current density of about $10^{-8}$ amperes per mm$^2$ is preferred.

It should be noted that the release of silver or other metal from the iontophoretic material need occur for only 3–6 months in order to prevent endophthalmitis. Accordingly the amount of such oligodynamic metals in the iontophoretic polymers is adjusted to assure depletion thereof from the polymer within approximately 3 to 6 months.

Although iontophoretic antimicrobial materials of the type shown by Milder are preferred, the invention may be practiced with other antimicrobial materials that are non-iontophoretic.

For example U.S. Pat. No. 5,520,664, issued to R. J. Bricault et al, discloses the concept of modifying solid polymers by incorporating antimicrobial metals onto or into their surfaces, with atoms of the antimicrobial metals being deposited onto or implanted into the polymer surfaces by an ion beam assisted deposition process ("IBAD"). Bricault et al show that biocompatible materials such as a polyester (e.g., "Dacron"), polyurethane, silicone and fluoropolymers (e.g., "Teflon") can be impregnated with an antimicrobial agent such as silver, through the IBAD process. Acrylic materials, e.g., PMMA, impregnated with antimicrobial metals according to the Bricault et al technique may be used for the optics if the resulting antimicrobial polymers are sufficiently clear and transparent to light. However, with respect to an embodiment as shown in FIG. 7, if the metal impregnation results in an opaque material, a masking procedure may be followed to limit the metal impregnation to the periphery of the optic. The same materials also may be used to form the haptics.

Although Bricault et al represent that their impregnated metals are non-leachable, for the purposes of this invention metals such as silver are considered to be leachable, since the patentees admit (column 12, lines 63–65) that silver and palladium are released in the order of 0.12 ppm. That amount closely approaches the amount of silver released from the iontophoretic polymers prepared by Milder, and is adequate for the purpose of killing bacteria in the surrounding medium of the eye.

Another group or source of antimicrobial materials suitable for this invention is disclosed by U.S. Pat. No. 4,723, 950, issued 9 Feb. 1988 to Clarence C. Lee. This patent discloses the concept of compounding an antimicrobial substance such as gentamicin, tetracycline or other antibiotic into a polymer such as polyproplyene, polyethylene, polysulfone or a silicone, and then coating the impregnated polymer with a hydrophilic material. Alternatively, a porous polymer such as polyethylene is impregnated with a hydrophilic polymer and at least one antimicrobial agent. Once immersed in an aqueous medium, the hydrophilic material swells to provide a controlled path for the drug to release into the surrounding environment. In the practice of this invention, polymer materials of the type disclosed by Lee are preferably used only to manufacture the haptic components, although they may be used for the optic if they are sufficiently transparent and provide the desired refractive index.

U.S. Pat. No. 5,340,581, issued 23 Aug. 1994 to M. M. Tseng et al, discloses an antimicrobial polymer composition that is suitable for fabricating the haptics of the IOL or else as a coating for the haptics. More specifically, Tseng et al provide a sustained release matrix that comprises (1) a support resin in the form of a water-insoluble polymer, (2) a water-soluble polymer and (3) an antimicrobial agent. For the purposes of this invention, the support resin may be PMMA, polypropylene, a silicone, or other water-insoluble polymer. The water soluble polymer may be of various compositions, including but not limited to those disclosed by Tseng et al. The antimicrobial agent may take various forms, including but not limited to those disclosed by Tseng et al, namely, chlorhexidine, tetracycline and domiphen bromide.

U.S. Pat. Nos. 5,358,688 and 5,536,861, both issued to J. Richard Robertson, disclose antimicrobial quaternary ammonium group-containing polymers. By way of example, the Robertson patents disclose organo-silicon polymers that comprise antimicrobial quaternary ammonium groups. These antimicrobial polymers are water soluble and are intended to be dissolved in a solution to form a liquid for disinfecting contact lenses. However, U.S. Pat. No. 5,358,688 also discloses (column 8, lines 51–61, and column 10, lines 24–39) that Robertson's antimicrobial polymers may take the form of higher molecular weight cross-linked polymers that may be used to form solid structures such as contact lenses. The antimicrobial polymers disclosed by Robertson may be used to form or to coat haptics according to this invention The information concerning antimicrobial compositions disclosed by said U.S. Pat. Nos. 5,520,664, 4,723,950, 5,358,688 and 5,536,861 is incorporated herein by reference thereto. It is appreciated that still other antimicrobial compositions known to persons skilled in the art also may be used in practicing this invention.

IOLs made according to this invention offer several advantages. The foremost advantage is that bactericidal potency is maximized because metal is guaranteed to go into solution as ions, thus producing a minimum ten-fold reduction in bacterial colonization rate. Also the iontophoresis current is self-generating and self-regulating. Furthermore, because the metal powders (electrodes) are dispersed substantially uniformly through the base polymer material, and because the current level is very low, galvanic anti-bacterial action remains functional for a relatively long period of time. A further advantage is that antimicrobial species is leachable into the aqueous environment immediately surrounding the surgical optical site, whereby to kill circulating organisms, and also is surface-active so as to prevent colonization of organisms on the surface of the IOLs.

Although the invention has been shown and described with respect to exemplary embodiments thereof, various other changes, omissions and additions in form and detail thereof may be made therein without departing from the spirit and scope of the invention. For example, part or all of each of the plate sections 8 of the IOL shown in FIG. 1 could be made of a black iontophoretic silicone material as described by the Milder patents cited hereinabove, while the optic body 6 could be co-molded of a non-antimicrobial clear transparent plastic. Similarly, the design of FIG. 6 could comprise an annular rim made of an opaque antimicrobial material with the haptics being formed integrally with and of the same antimicrobial material as the rim, and a transparent center optical zone in the form of a circular disk of clear PMMA that is surrounded by and secured to the rim. Still other modifications will be obvious to persons skilled in the art.

What is claimed is:

1. An intraocular lens comprising an optic lens body and lens positioning means extending laterally from said lens body, at least a portion of said intraocular lens being made of an antimicrobial iontophoretic polymer material that comprises a polymer matrix, a first material having a first galvanic electric potential, and a second material having a second galvanic electric potential, said first and second materials being dispersed in said polymer matrix, and said polymer matrix comprising a polymer having a predetermined electrical resistivity and controlling current flow produced between said first and second materials when said antimicrobial iontophoretic polymer material is contacted with saline fluid in a mammalian eye.

2. An intraocular lens according to claim 1 wherein said antimicrobial iontophoretic polymer material has a polymer matrix composed of polyethylene, polypropylene, PMMA and/or silicone, and said first and second materials are metal particles of silver and platinum.

3. An intraocular lens according to claim 1 wherein said lens positioning means is composed of said antimicrobial iontophoretic polymer material.

4. An intreocular lens according to claim 1 wherein said optic lens body comprises a rim section and a lens section surrounded by said rim section, and further wherein said rim section is composed of said antimicrobial iontophoretic polymer material.

5. An intraocular lens according to claim 1 wherein said lens is foldable.

6. An intraocular lens according to claim 1 wherein at least a first portion of said lens is made of PMMA.

7. An intraocular lens comprising a plastic optic portion that is characterized by a lens and at least one haptic or plate portion affixed to and extending away from said optic portion, said at least one haptic or plate portion being composed of an antimicrobial polymer.

8. An intraocular lens characterized by a lens portion and at least one haptic portion affixed to and extending away from said optic portion, at least said haptic portion being composed of an antimicrobial polymer.

9. An intraocular lens according to claim 8 wherein said antimicrobial polymer has an iontophoretic structure comprising a first material having a first galvanic electric potential, a second material having a second galvanic electric potential, and a conductive polymer, said first and second materials being dispersed in and separated by said conductive polymer, said conductive polymer having a predetermined resistivity and controlling a current flow produced between said first material and said second material when said iontophoretic structure is in contact with saline fluid in a mammalian eye.

10. An intraocular lens according to claim 9 wherein said first material comprises silver and said second material comprises platinum.

11. An intraocular lens according to claim 9 wherein said first material comprises silver and said second material comprises copper.

12. An intraocular lens according to claim 9 wherein said conductive polymer is a member of the group consisting of an acrylic polymer, a vinyl polymer, a polyester, a silicone, a polyurethane, polyethylene, polypropylene and polyvinylidene fluoride.

13. An intraocular lens according to claim 12 wherein said first and second materials are metal powders.

14. An intraocular lens comprising a plastic optic portion that is characterized by a lens and at least one haptic portion affixed to and extending away from said optic portion, said at least one haptic portion being composed of an antimicrobial polymer.

15. An intraocular lens according to claim 14, wherein said optic portion comprises a rim section and a lens section surrounded by said rim section, and further wherein said rim section comprises an antimicrobial polymer.

16. An intraocular lens comprising an optic lens body and lens positioning means extending laterally from said lens body, at least a portion of said intraocular lens being composed of an antimicrobial polymer structure comprising a polymer having metal atoms dispersed therein.

17. An intraocular lens comprising a lens body and lens positioning means extending laterally from said lens body, and an antimicrobial iontophoretic polymer coating on a portion of said intraocular lens, said iontophoretic polymer coating comprising a first material having a first galvanic electric potential, a second material having a second galvanic electric potential, and a conductive polymer, said first and second materials being dispersed in and separated by said conductive polymer, said conductive polymer having a predetermined resistivity and controlling a current flow produced between said first material and said second material when said iontophoretic structure is in contact with saline fluid in a mammalian eye.

18. An intraocular lens according to claim 17 wherein said antimicrobial iontophoretic polymer coating is on said lens positioning means.

* * * * *